United States Patent [19]

Sato et al.

[11] Patent Number: 4,685,335

[45] Date of Patent: Aug. 11, 1987

[54] METHOD AND APPARATUS FOR MONITORING CRACKS OF A ROTATABLE BODY

[75] Inventors: Kazuo Sato, Kitaibaraki; Kouki Shiohata, Ohmiya; Osami Matsushita, Tomobe; Katsuaki Kikuchi, Tsuchiura; Masakazu Takasumi, Juoh; Ichiya Sato; Ryoichi Kaneko, both of Hitachi, all of Japan

[73] Assignee: Hitachi, Ltd., Tokyo, Japan

[21] Appl. No.: 681,576

[22] Filed: Dec. 14, 1984

Related U.S. Application Data

[63] Continuation of Ser. No. 471,807, Mar. 3, 1983, abandoned.

[30] Foreign Application Priority Data

Mar. 3, 1982 [JP] Japan ................................. 57-34414

[51] Int. Cl.⁴ ............................................. G01N 29/04
[52] U.S. Cl. ........................................ 73/660; 73/587; 364/508
[58] Field of Search ................. 73/659, 660, 801, 587; 364/508; 340/683

[56] References Cited

U.S. PATENT DOCUMENTS

| | | | |
|---|---|---|---|
| 3,705,516 | 12/1972 | Reis | 73/660 |
| 4,352,293 | 10/1982 | Kurihara et al. | 73/660 |
| 4,366,544 | 12/1982 | Shima et al. | 73/660 |
| 4,377,947 | 3/1983 | Matsushita et al. | 73/660 |
| 4,380,172 | 4/1983 | Imam et al. | 73/659 |
| 4,425,798 | 1/1984 | Nagai et al. | 73/659 |
| 4,429,578 | 2/1984 | Darrel et al. | 73/660 |
| 4,435,770 | 3/1984 | Shiohata et al. | 364/508 |

FOREIGN PATENT DOCUMENTS 54-147882 11/1979 Japan ...................................... 73/660

OTHER PUBLICATIONS

"Vibrations in Cracked Shafts," Henry et al, *Conference on Vibrations in Rotating Machinery*, C162/76, Sep. 1976, I.M.E.
"Dynamic Behavior of a Simple Rotor with a Cross-Sectional Crack", Gasch, *Conference on Vibrations in Rotating Machinery*, C178/76, Sep. 1976, I.M.E.
"The Vibrational Behavior of a Rotating Shaft System Containing a Transverse Crack," Mayes et al, *Conf. on Vibrations in Rotating Machinery*, C168/76, Sep. 1976, I.M.E.
"Vibrational Behavior of a Turbine Rotor Containing a Transverse Crack", Grabowski, *Transactions of the ASME*, vol. 102, Jan. 1980, pp. 140–146.

*Primary Examiner*—Howard A. Birmiel
*Attorney, Agent, or Firm*—Antonelli, Terry & Wands

[57] ABSTRACT

A method and apparatus for monitoring cracks of a rotatable body by detecting cracks by measuring accoustic emission signals and evaluating the depth of cracks from the result of the comparison of assumed vibrations of the rotatable body and its measured vibrations. By this method and apparatus not only the beginning of cracking of the rotatable body, but also the progress of cracking on an online basis can be detected and monitored.

18 Claims, 7 Drawing Figures

METHOD AND APPARATUS FOR MONITORING CRACKS OF A ROTATABLE BODY

This is a continuation of application Ser. No. 471,807 filed Mar. 3, 1983, now abandoned.

BACKGROUND OF THE INVENTION

The present invention relates to a method and apparatus for monitoring cracks of a rotatable body.

A rotatable body forming a part of a rotary machine can be cracked due to, for example, creep fatigue or stress corrosion with such cracks causing, for example, operational disturbances, machine breakdowns, or the like thereby present serious and dangerous situations for operating personnel, especially with turbine motors of thermal or nuclear power generation equipment. Consequently, it is imperative that measures should be taken to avoid in advance any accidents which may occur as a result of cracks in the rotatable body of the rotary machine and an effective repair of the rotatable body should be facilitated.

Conventionally, in order to monitor cracks, acoustic emission signals, hereinafter referred to as AE signals, generated by a cracking in a rotatable body such as a rotor have been detected; however, in the conventional methods, it is impossible to monitor the progress of cracking. While it has been proposed to detect vibration signals of the rotatable body and then to monitor cracks by utilizing the AE signals, a detection of cracks according to this proposal is restricted because the cracks can be detected only if the speed of the rotatable body is changed and if the size of the cracks exceeds a predetermined value.

An object of the present invention resides in providing a method and apparatus for detecting a cracking of a rotatable body and for monitoring the progress of such cracking.

This object if achieved according to the invention by a method for monitoring cracks of a rotatable body comprising the steps of detecting cracks by measuring accoustic emission signals, measuring vibrations of the rotatable body, calculating the position of cracks on the basis of the measured accoustic emission signals, comparing assumed vibrations with measured vibrations and evaluating the depth of cracks from the result of this comparison.

Hereby, it is possible to detect the beginning of cracking of a rotatable body very quickly and also to monitor accurately the progress of cracking on an on line basis because not only accoustic emission signals but also vibration signals are measured and the depth of cracks can be evaluated on the basis of the result of comparison of assumed vibrations and measured vibrations.

Preferably, the detecting of cracks by measuring accoustic emission signals is perfomred by detecting first accoustic emission signals from two first accoustic emission detectors attached to the rotatable body, detecting second accoustic emission signals from two second accoustic emission detectors attached to the bearings of the rotatable body and by eliminating accoustic emission signal portions caused by other reasons than cracking from those accoustic emission signals. According to this method, cracking can be detected accurately.

Other advantages and optional features of the present invention will become more apparent from the following description when taken in connection with the accompanying drawings which show, for the purpose of illustration only, several embodiments in accordance with the present invention.

Figure 1:
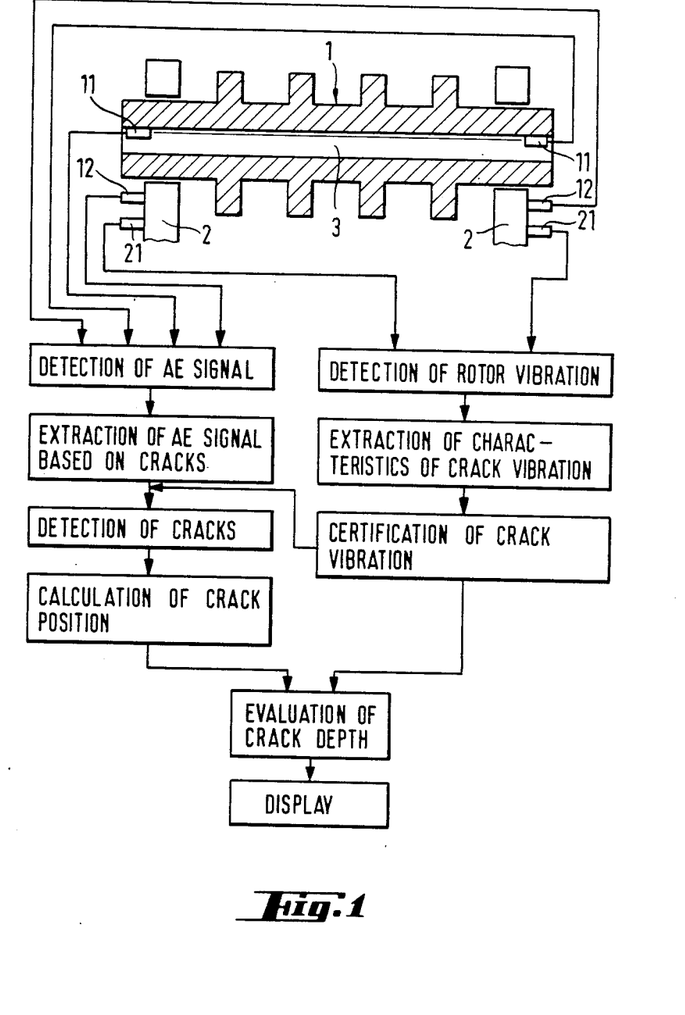
FIG. 1 is a schematic view of an arrangement in accordance with the present invention for monitoring cracks in a rotor.

Referring now to the drawings wherein like reference numerals are used throughout the various views to designate like parts and, more particularly, to FIG. 1, according to this figure, a rotor 1 is rotatably supported by bearings 2 at both ends thereof, with a pair of first AE detectors 11 being disposed inside a central bore 3 of the rotor 1 so as to directly detect a AE signal propagating within the rotor 1 from a position of the cracks, and a pair of second AE detectors 12 disposed at the bearings 2 so as to indirectly detect the AE signal propagated from the rotor 1 to the bearings 2 through an oil film of the bearings 2.

The AE signals detected may also include AE signal portions caused by reasons other than cracks such as, for example, rubbing and bearing damages; therefore, authentic or actual AE signals derived from cracks must be extracted from the overall detected AE signals.

In this connection, rubbing means that the rotating rotor and the immovable portion of the bearings contact each other, and even a slight rubbing may cause the generation of a AE signal. A bearing damage is classified as a metal wiping and a partial direct contact between the rotating and immovable parts of the bearing, with the metal wiping meaning a slipping between the rotor journal and rotating parts of the bearing under an excess bearing load or high temperature of the bearing lubricating oil creating a AE signal even from an early stage. The above noted partial direct contact means that the rotating and immovable parts of the bearings contact each other near the end of the bearing and create a AE signal although the amount thereof may not be as large as the above-noted types of AE signals.

The AE signals caused by reasons other than cracking have characteristic phenomenas and for example, the AE signal caused by rubbing has the same period as the rotation period of the rotor. Therefore, it is possible to make a histogram of this AE signal, for example, an AE signal caused by rubbing can be recognized by a histogram circuit provided in an AE signal processing circuit.

An AE signal caused by metal wiping is cyclic and the amplitude of the detected AE signals is slowly rising. Therefore, for example, this AE signal can be recognized by a counter circuit counting the number of AE signals the amplitude of which exceeds a predetermined value.

In case of the partial direct contact a low frequency signal is overlaid by high frequency noise. Therefore, this AE signal can be recognized by the increase or decrease of the AE signal after having passed a bandpass filter ranging from 20 to 200 Hz.

Due to the place of rubbing and bearing damages AE signals caused hereby can be detected most accurately at the bearings. If the first AE signal is detected at the rotor by detector 11 and if the second AE signal is not detected at the bearing by detector 12, the first AE signal corresponds to cracking. Even in case that cracking happens at the same time as rubbing and bearing damages, cracking can be detected by deleting AE signal portions caused by rubbing and bearing damages.

Following detection of cracking, its position is evaluated. This is done by calculating the time difference between two AE signals detected by the two detectors 11 which are disposed at both ends of the rotor 1 in the following manner.

The distance l of a crack from a middle of the pair of AE detectors 11 may be determined by the following equation:

ti $1 = (V \cdot \Delta t)/2$;

wherein:

$\Delta t$ = a time difference between two AE signals detected by the two AE detectors 11 disposed at both ends of the rotor 1; and $V$ = a propagating velocity of the AE signal.

Hereafter, the depth of the cracks can be estimated based on a comparison of the vibration signal measured by vibration detectors 21 disposed at the bearings 2 as shown in FIG. 1 with a calculated vibration signal. The calculation of the calculated vibration signal is based on the position of a crack according to equation (1) and of assumed crack depths. If the difference between the calculated and the measured vibration signals does not exceed a predetermined value, the assumed crack depth can be considered as authentic depth. If the difference exceeds the predetermined value, the calculation is repeated by changing the assumed depth until the difference is smaller than the predetermined value. In calculating vibration signals in practice, linearized calculating methods may be used by proper approximation because vibration of a rotor having cracks includes not only the basic frequency component but also harmonic components.

For calculating, some positions of the rotor 1 in axial direction are chosen. Furthermore, two vibration amplitudes x, y perpendicularly intersecting each other are approximated in the following manner. The vibration signal is calculated by repeated numeral approximation calculation taking into consideration parameters like dimensions of the rotor, inherent constants of rotor material, depth and position of cracks and the like.

$$x = X_0 + \tfrac{1}{2}(X_1 \epsilon^{i\omega\tau} + \overline{X_1}\epsilon^{-i\omega\tau}) + \tfrac{1}{2}(X_2 \epsilon^{i\omega\tau} + \overline{X_2}\epsilon^{-2\omega\tau}) +$$
$$\tfrac{1}{2}(X_3 \epsilon^{i\omega\tau} + \overline{X_3}\epsilon^{-i3\omega\tau})$$

$$y = y_0 + \tfrac{1}{2}(y_1 \epsilon^{i\omega\tau} + \overline{y_1}\epsilon^{-i\omega\tau}) + \tfrac{1}{2}(y_2 \epsilon^{i2\omega\tau} + \overline{y_2}\epsilon^{-i2\omega\tau}) +$$
$$\tfrac{1}{2}(y_3 \epsilon^{i3\omega\tau} + \overline{y_3}\epsilon^{-i3\omega\tau})$$

$i = \sqrt{-1}$: imaginary number unit
$\omega$: angular acceleration of the rotor
$x_0, y_0$: stationary deflection of the rotor
$x_1, x_2, x_3; y_1, y_2, y_3$: vector of vibration component (suffix represents harmonics)
$\overline{x_1}, \overline{x_2}, \overline{x_3}; \overline{y_1}, \overline{y_2}, \overline{y_3}$: complex vector of vibration component.

High frequency components are characteristic for the vibration of a rotor having cracks and their amplitudes generally tend to increase in accordance with the progress of cracking, i.e. with the increase of crack depth. Therefore, it is preferred to compare measured vibration signals with calculated vibration signals not only in an overall manner but with respect to each harmonic component including basic frequency component. In practice, basic frequency and first and second harmonic components are compared because vibration components of the third and further harmonics are small.

Before cracking occurs specific vibration signals are measured. When cracking occurs, those specific vibration signals are substracted from the then measured vibration signals to give the vibration signal only caused by cracking.

As mentioned above, since the vibration of a rotor having cracks includes components of high harmonics of integral multiples of the rotation speed of the rotor, it is possible to confirm cracking by checking the existence of components of high harmonics. The detected rotor vibration is analyzed with respect to each integral multiple of the rotation speed. Any change of components of basic frequency and first and second harmonics from each initial state is investigated.

If there exists any change, there is the possibility of cracking. This result is useful to check cracking detected from the AE signal as described above. By this way, reliability of detection of cracking can be improved.

A further detailed embodiment is described below.

The first AE detector 11 and a transmitter 13 are disposed at both end portions and inside the central boring 3 of the turbine rotor 1 which is rotatably supported by a pair of bearings 2. The second AE detector 12 and the vibration detector 21 are disposed at the bearings 2. The first AE signal detected by AE detector 11 is amplified and is frequency modulated by transmitter 13 and is transmitted as frequency modulated signal from transmitting antenna 14a. This signal received by antenna 14b is amplified by receiver 16. The receiving antenna 14b is located at a non-rotatable area. The signal is then coupled to an AE signal processing device 17. The output signals $S_{1L}$, $S_{1R}$ of receivers 16 correspond to AE detector 11 located on the left side and right side in FIG. 2, respectively. On the other hand, the second AE signals detected by AE detectors 12 are amplified by amplifiers 15 and coupled to AE signal processing device 17.

Figure 2:
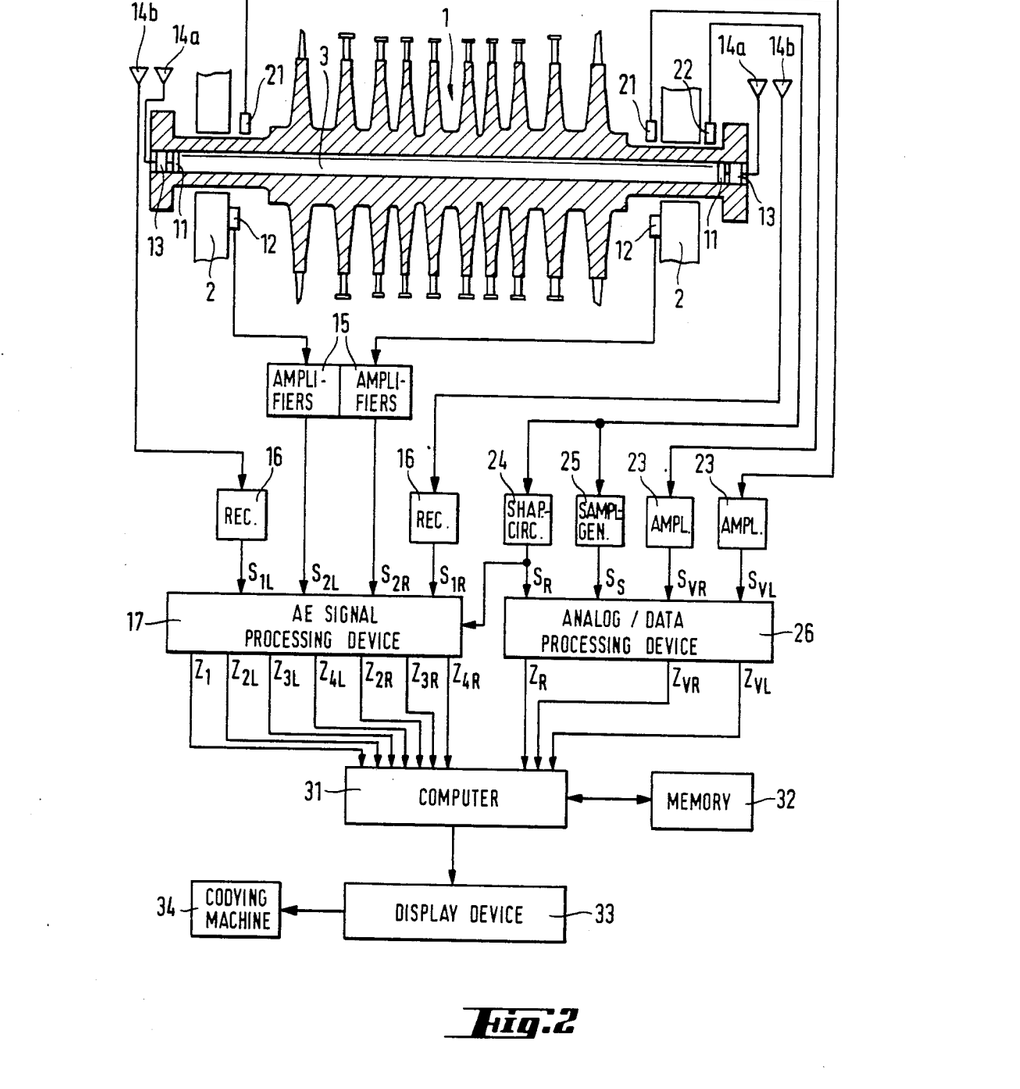
FIG. 2 is a block diagram of an apparatus for monitoring cracks constructed in accordance with the present invention.

The output signals $S_{2L}$, $S_{2R}$ of amplifiers 15 correspond to AE detectors 12 located on the left side and the right side in FIG. 2, respectively.

Figure 3:
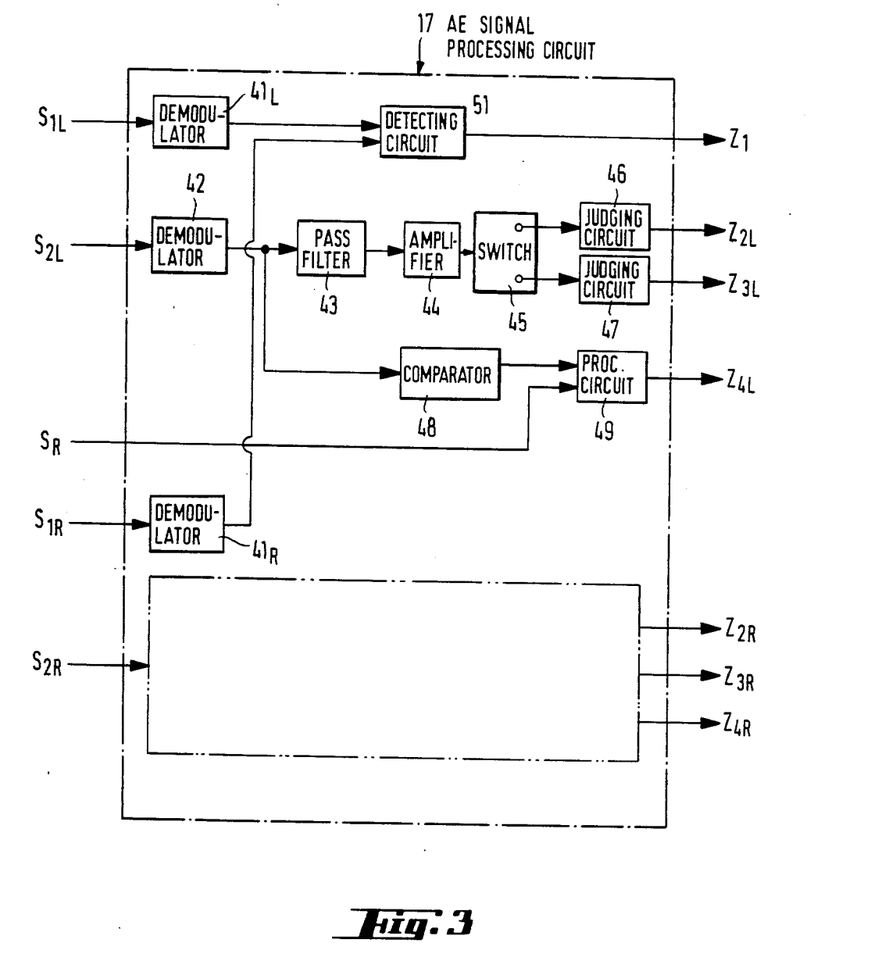
FIG. 3 is a block diagram of a signal processing device of the apparatus of FIG. 2.

As shown in FIG. 3, AE signals $S_{1L}$, $S_{1R}$ are demodulated by demodulators $41_L$, $41_R$, respectively. The time difference $\Delta t$ is calculated from these two signals in time difference detecting circuit 51 and the calculated signal is introduced as input signal $Z_1$ to a computer 31. AE signal $S_{2L}$ is demodulated by demodulator 42 and coupled to a change over switch 45 through low pass filter 43 and amplifier 44. This switch 45 is changed according to the rotation speed of the rotor, that is, this switch 45 is coupled to a metal wiping judging circuit 46 in case of low speed operation in which the speed is very low like several revolutions per minute or coupled to partial direct contact judging circuit 47 in case of high speed operaion.

The output signals $Z_{2L}$, $Z_{3L}$ of the metal wiping judging circuit 46 and partial direct contact judging circuit 47, respectively, are coupled to the computer 31.

Low pass filter 43 is effective in extracting the AE signal caused by bearing damages. The bandpass of this filter includes a range from 20 to 200 Hz. Further, the output of the demodulator 42 is coupled to level comparator 48 and the output of the comparator 48 is processed in a histogram processing circuit 49 and is connected to the computer 31 as signal $Z_{4L}$. Signal $S_R$ which is originally the signal of a rotation pulse detector 22 has been shaped in shaping circuit 24 and is coupled to the histogram processing circuit 49 as histogram processing signal. The AE signal processing circuit 17 includes circuits 42 to 49 to process signal $S_{2R}$. In these circuits signals $Z_{2R}$, $Z_{3R}$, $Z_{4R}$ corresponding to signals $Z_{2L}$, $Z_{3L}$, $Z_{4L}$ respectively are obtained and coupled to the computer 31.

On the other hand, the rotor vibration signal is detected by the vibration detector 21 disposed at the bearing 2 and amplified by amplifiers 23. Signals $S_{VL}$ and $S_{VR}$ correspond to vibration signals from the bearings 2 on the left side and the right side of the rotor, respectively. Sampling signal generator 25 is a generator which receives a pulse signal of 1 pulse per rotation from rotation pulse generator 22 and samples vibration signals $S_{VL}$, $S_{vR}$ simultaneously with the rotation of the rotor. This sampling generator 24 generates a sampling signal $S_S$ proportional to the rotation speed of the rotor.

Analog vibration signals $S_{VL}$, $S_{VR}$ are converted to digital signals according to the instruction of the sampling signal generator in an analog data processing device 26 which consists of an A/D converter and a low pass filter. Thus, signals $S_{VL}$ and $S_{VR}$ become input signals $Z_{VL}$, $Z_{VR}$ to the computer 31. Shaping circuit 24 converts one pulse per revolution of rotation pulse detector 22 to a sin wave and amplifies this wave and makes phase standard signal for analyzation of vibration. This analog phase standard signal $S_R$ is converted to a digital signal in the analog data processing device 26 and afterwards coupled to the computer 31 as signal $Z_R$.

In the computer 31 it is diagnosed, based on AE and vibration signals, whether or not there is cracking of the rotor. Its result is presented on a display device 33 such as a cathode ray tube. If necessary, the result is recorded by a copying machine 34. The diagnosis of a crack is carried out by diagnosis software prestored in a memory 32 of the computer.

Figure 4:
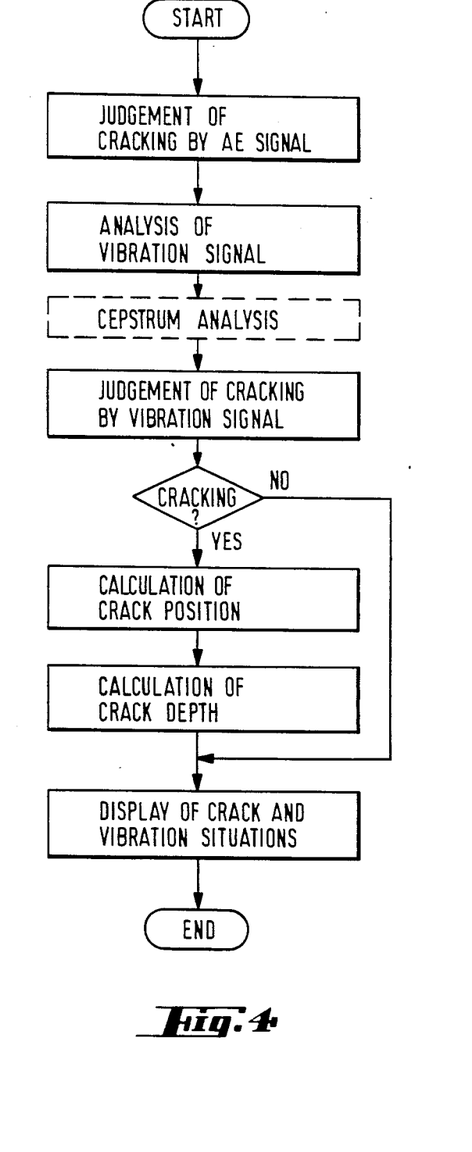
FIG. 4 is a flow chart of diagnostic software for the method of the present invention.

First of all, checking of cracking by AE signal is done, as schematically shown in the flow chart of FIG. 4. For example, if each signal $Z_1$, $Z_{2L}$, $Z_{3L}$, $Z_{4L}$, $Z_{2R}$, $Z_{3R}$ and $Z_{4R}$ is zero, there is no cracking. In case that $Z_1$ is zero or extremely small and at least one of the signals $Z_{2L}$, $Z_{3L}$, $Z_{4L}$, $Z_{2R}$, $Z_{3R}$ and $Z_{4R}$ is generated, there is no cracking, but the AE signal is caused by other reasons than cracking, for example, if only signal $Z_{4L}$ is generated, rubbing exists near AE signal detector 12.

Following the above checking, vibration analysis on vibration signals $Z_{VL}$, $Z_{VR}$ is performed by using Fourier analysis and its result is standarized according to the harmonics of the rotation speed.

Thus, vibration components of the basic frequency and up to the fourth harmonic are diagnosed and changes of these components from the initial state stored in memory 32 in advance are calculated for each harmonic in order to detect cracking. If the amount of the changes exceeds a perdetermined value, there is the possibility of cracking. Further, in detail, cracking can be checked as follows. If both results by AE signal and vibration signal show the possibility of cracking, these results are regarded as cracking. If both results do not show the possibility, it is regarded that cracking does not occur. If each result is different, priority to decide cracking is given to the result by the AE signal. In this case, however, it is more preferable that the same check by the AE signal and the vibration signal is repeated by changing the data to the computer again to avoid misjudgement due to signal noise, and if the same result is obtained in checking twice, such result is adapted as a correct one. The number of repetitions may be more than two.

In case of cracking, the position of a crack is calculated based on equation (1). Following this, the depth of the crack in the calculated position is assumed and the vibration signal correspondingly calculated. The dimensions of the rotor, inherent characteristics and data of rotor material and inherent characteristics of the bearings are prestored in the memory.

Figure 5:
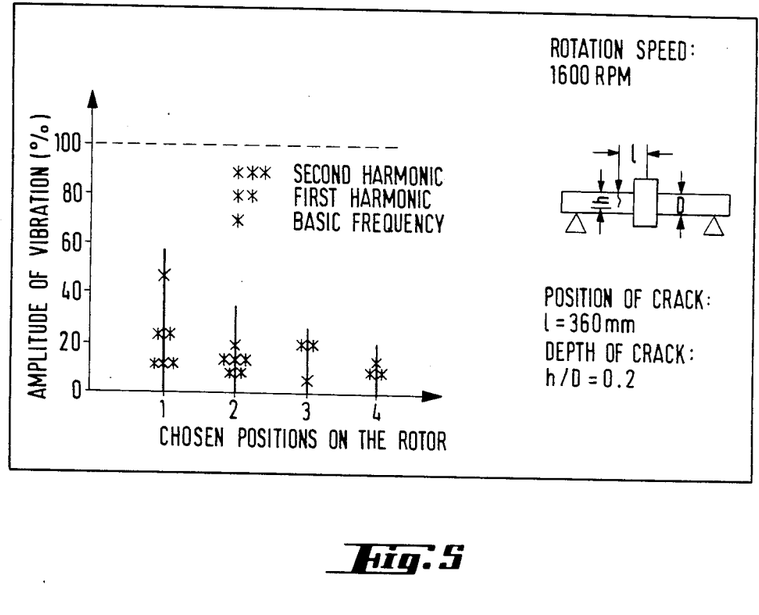
FIG. 5 is a display of a diagnostic result obtained by the method of the present invention.

Cracking and vibration situations can be displaced properly, for example a diagnosis result of a model rotor is shown in FIG. 5. In FIG. 5, the position of a crack is shown on the right side and the amplitude of vibration at chosen positions on the rotor on the left side. The content of this display is renewed on an online basis. Even if cracking does not occur vibration signals are shown on the display. Therefore, usually this display has the function as a vibration monitor.

Figure 6:
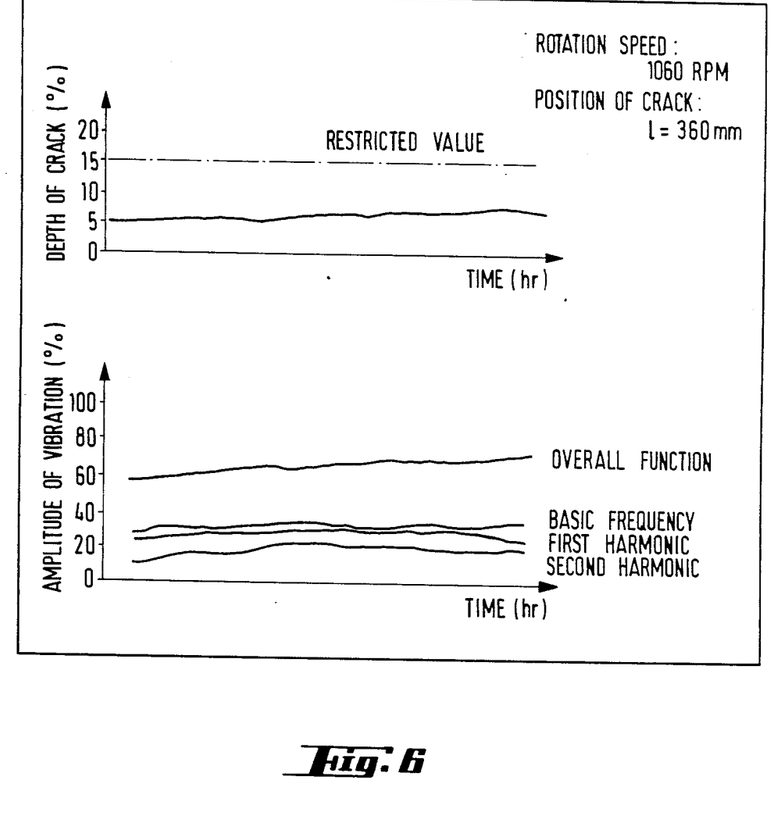
FIG. 6 is another example of a display of a diagnostic result obtained by the method of the present invention.

FIG. 6, the progress of cracking dependent on time is displayed. In FIG. 6, the depth of a crack and the amplitude of vibration at chosen positions are shown as time proceeds. It is possible to estimate the time period in which cracking will exceed a restricted value of crack depth in which case repair becomes necessary.

Figure 7:
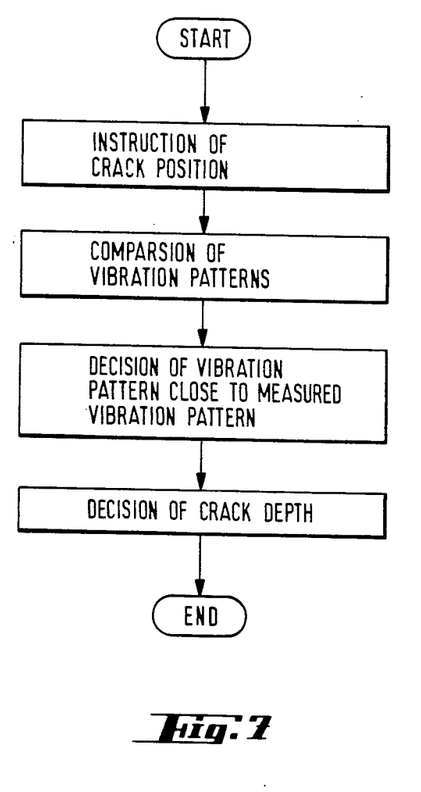
FIG. 7 is a flow chart of another method for monitoring a depth of cracks in a rotating body in accordance with the present invention.

FIG. 7 shows another way of estimating the depth of crack. In this embodiment, the actually measured vibration pattern is compared with predetermined vibration pattern, consisting of a relationship between the amplitudes of vibration of basic frequency and harmonic components and the depth of crack (compare following Table 1) prestored in the memory 32 in advance. The crack depth can be determined or evaluated by choosing the pattern in which the difference between the amplitudes of each component of the measured vibration pattern and the perdetermined vibration pattern is minimum or in which the difference of the ratio of the amplitudes of different basic frequency and harmonic components of the measured vibration pattern and the predetermined vibration pattern is minimum. A predetermined vibration pattern consists of the amplitudes of basic frequency and first and second harmonic components in Table 1. The values as shown in Table 1 are determined in advance according to the predetermined rotor speed and predetermined crack position.

TABLE 1

| | Position of crack 1 = 360 mm | | |
| | amplitude of vibration (μm) | | |
| depth of crack (h/D) | basic frequency | first harmonic | second harmonic |
| --- | --- | --- | --- |
| under 0,05 | 10 | 2 | — |
| under 0,1 | 21 | 7 | 3 |

TABLE 1-continued

| | Position of crack 1 = 360 mm | | |
| --- | --- | --- | --- |
| | amplitude of vibration (μm) | | |
| depth of crack (h/D) | basic frequency | first harmonic | second harmonic |
| under 0.2 | 36 | 17 | 10 |
| under 0.3 | 46 | 20 | 13 | h: depth of crack
D: diameter of the rotor at the crack position

According to these embodiments cracking can be detected quickly and accurately, and also the crack depth can be estimated on line. Therefore, serious accidents by cracks can be avoided in advance and planned maintenance of rotor becomes possible.

We claim:

1. A method for monitoring cracks of a rotatable body, the method comprising the steps of detecting cracks by measuring acoustic emission signals, measuring vibrations of the rotatable body, calculating the position of the cracks on a basis of the measured acoustic emission signal, comparing assumed variations with the measured vibrations and evaluating the depth of cracks from the result of this comparison, and wherein the step of detecting of cracks by measuring acoustic emission signals is performed by detecting first acoustic emission signals from two first acoustic emission detectors attached to the rotatable body, detecting second acoustic emission signals from two second acoustic emission detectors attached to bearings of the rotatably body and by eliminating acoustic emission signal portions caused by reasons other than cracking from those acoustic emission signals.

2. A method according to claim 1, wherein the accoustic emission signal portions caused by other reasons than cracking are detected by passing the overall accoustic emission signals through a histogram circuit, a counter circuit and a bandpass filter ranging from 20 to 200 Hz.

3. A method according to claim 1, wherein the assumed vibrations are predetermined vibration patterns of the amplitudes of basic frequency and harmonic components.

4. A method according to claim 1, wherein the detecting of cracks by measuring accoustic emission signals is checked by measured vibration signals based only on cracks.

5. An apparatus for monitoring cracks of a rotatable body comprising a first pair of accoustic emission detectors attached to the rotatable body, a second pair of accoustic emission detectors attached to the bearings of the rotatable body, means for detecting cracks by extracting accoustic emission signals caused by cracks, means for calculating the position of cracks based on the time difference between the accoustic emission signals from the detectors of the first pair, means for comparing assumed vibrations with measured vibrations, means for evaluating the depth of cracks from the result of this comparison and means for displaying the cracks.

6. An apparatus according to claim 5 comprising transmitters attached to the rotatable body to transmit the first accoustic emission signals from the detectors of the first pair to receivers disposed at a non-rotatable area, first amplifiers to amplify the second accoustic emission signals from the second pair of accoustic emission detectors, a rotation detector to detect the rotation of the rotatable body, a shaping circuit to shape the output of the rotation detector, a sampling generator to generate a sampling signal from the output of the rotation detector, vibration detectors attached to the bearings of the rotatable body to detect vibrations of the rotatable body, second amplifiers to amplify the output signals of the vibration detectors, accoustic emission signal processing device to process the output signals of the receivers, the first amplifiers and the shaping circuit, an analog data processing device to process the output signals of the shaping circuit, the sampling generator and the second amplifiers, a computer to evaluate the depths of cracks on the basis of the output signals of the accoustic emission signal processing device and the analog data processing device and to transmit the evaluated depth of the cracks to the display means.

7. An apparatus according to claim 5 wherein the first pair of accoustic emission detectors are disposed inside a central boring of the rotatable body.

8. A method, for monitoring cracks of a rotatable body, the method comprising the steps of detecting cracks by measuring acoustic emission signals, measuring vibrations of the rotatably body, calculating the position of cracks on the basis of the measured acoustic emission signals, comparing assumed vibrations with the measured vibrations and evaluating the depth of cracks from a result of this comparison, when the measured acoustic emission signals include two signals detected at two axially spaced positions of the rotatable body, the position of the cracks is calculated on the basis of the time difference between the two signals, the assumed vibrations of the rotatable body are calculated on the basis of the calculated position of the cracks and of the assumed depths of the cracks, and wherein the detecting of cracks by measuring acoustic emission signals is performed by detecting first acoustic emission signals from two first acoustic emission detectors attached to the rotatable body, detecting second acoustic emission signals from two second acoustic emission detectors attached to the bearings of the rotatable body and by eliminating acoustic emission signal portions caused by other reasons than cracking from those acoustic emission signals.

9. A method according to claim 8, wherein the accoustic emission signal portions caused by other reasons than cracking are detected by passing the overall accoustic emission signals through a histogram circuit, a counter circuit and a bandpass filter ranging from 20 to 200 Hz.

10. A method for monitoring cracks of a rotatable body, the method comprising the steps of:
measuring two acoustic emission signals at two axially spaced positions of the rotatable body;
determining a position of cracks of said rotatable body as a function of a time difference between receipt of said two acoustic emission signals;
measuring vibrations of the rotatable body;
comparing the measured vibrations with predetermined vibrations for cracks of a known depth at the determined position of the cracks; and
repeating the comparison by changing the predetermined vibration of cracks of known depth until the difference between the measured vibrations and the predetermined vibrations of cracks of a known depth fall within an acceptable value to thereby determine the actual depth of said cracks.

11. The method according to claim 10, further including the steps of:

determining an actual crack depth on a basis of the assumed crack depth which meets said condition.

12. The method according to claim 11, wherein said acoustic emission portion caused by sources other than cracks in said rotatable body are produced by passing said two acoustic emission signals through a histogram circuit, a countercircuit and a band pass filter having a band pass ranging from 20-200 Hz.

13. The method of claim 10 further including the steps of:
measuring two primary acoustic emission signals by two detectors attached to the rotatable body;
measuring two secondary acoustic emission signals by two detectors attached to bearings supporting the rotatable body; and
combining said two primary acoustic emission signals and said two secondary acoustic emission signals to produce two acoustic emission signals free of acoustic emission signal portions caused by sources other than acoustic emission signals caused by cracks in said rotatable body.

14. The method according to claim 10, wherein the predetermined vibrations are predetermined vibration patterns of amplitude of a fundamental frequency and harmonic frequencies.

15. An apparatus for determining a positioning and depth of cracks in a rotating body, the apparatus comprising detector means including two detectors axially spaced along said rotating body for producing two acoustic emission signals, first means for determining a location of cracks in said rotating body by comparing a time difference between receipt of the two acoustic emission signals to each of said two spaced apart detectors; vibration detecting means for producing vibration signals caused by cracks in said rotating body; second means for comparing predetermined vibration signals representing cracks of a known depth with said vibration signals, said second means repeatedly selecting different predetermined vibration signals with said vibration signals until a difference therebetween is within a predetermined value to thereby determine the actual depth of said cracks in said rotating body.

16. The apparatus according to claim 15, wherein said two detectors are located in contact with said rotating body and said detector means includes two additional acoustic emission signal detectors in contact with bearings supporting said rotating body, the output of said two detectors and from said two additional detectors being combined so that said two acoustic emission signals are free of acoustic emission portions which are not caused by cracks in said rotating body.

17. The apparatus of claim 15, wherein secondary acoustic emission signals are produced which are caused by sources other than cracks in said rotating body by feeding said two acoustic emission signals through a histogram circuit, a counter circuit and a band pass filter having a band pass ranging from 20-200 Hz.

18. The apparatus according to claim 15, wherein said predetermined vibration signals are predetermined vibration signal patterns, and wherein said apparatus further includes a memory means for storing said predetermined vibration signal patterns.

* * * * *